United States Patent
Hernández Pérez et al.

(10) Patent No.: US 7,423,429 B2
(45) Date of Patent: Sep. 9, 2008

(54) APPARATUS AND ASSOCIATED METHOD THAT INTEGRATE THE MODALITIES OF DIAGNOSIS AND THERAPY TO TREAT, IN PRINCIPLE, PATHOLOGIES GENERICALLY IDENTIFIED AS CANCER AND HIV/AIDS

(76) Inventors: Lázaro Eusebio Hernández Pérez, Dr. Juán Navarro 182 E-301, col. Doctores, Cuauhtemoc (MX) 06720; José Luis Jorge De Moral Más, Calle D #9, Manzana. III, Col. Educación, Coyoacan (MX) 04400

( * ) Notice: Subject to any disclaimer, the term of this patent is extended or adjusted under 35 U.S.C. 154(b) by 0 days.

(21) Appl. No.: 10/579,752

(22) PCT Filed: Nov. 28, 2003

(86) PCT No.: PCT/MX03/00105

§ 371 (c)(1),
(2), (4) Date: May 18, 2006

(87) PCT Pub. No.: WO2004/098408

PCT Pub. Date: Nov. 18, 2004

(65) Prior Publication Data

US 2007/0080688 A1    Apr. 12, 2007

(51) Int. Cl.
*G01V 3/00* (2006.01)
*A61B 5/055* (2006.01)

(52) U.S. Cl. .............. 324/309; 324/310; 324/314; 324/315; 324/318; 324/307; 600/411; 600/413; 600/422; 600/427; 600/428

(58) Field of Classification Search ......... 324/300–322; 600/407–435
See application file for complete search history.

(56) References Cited

U.S. PATENT DOCUMENTS

| 5,690,109 | A | | 11/1997 | Govind et al. ............ 600/411 |
| 5,919,135 | A | * | 7/1999 | Lemelson ................. 600/407 |
| 6,128,522 | A | * | 10/2000 | Acker et al. ............. 600/411 |
| 6,374,132 | B1 | * | 4/2002 | Acker et al. ............. 600/411 |
| 6,516,211 | B1 | * | 2/2003 | Acker et al. ............. 600/411 |
| 6,584,337 | B2 | | 6/2003 | Dumoulin ................. 600/410 |
| 6,773,408 | B1 | * | 8/2004 | Acker et al. ................ 601/2 |
| 7,048,716 | B1 | * | 5/2006 | Kucharczyk et al. ... 604/164.01 |
| 2007/0080688 | A1 | * | 4/2007 | Perez et al. .............. 324/318 |

FOREIGN PATENT DOCUMENTS

| CN | 1077655 | 10/1993 |
| JP | 2003/305019 | 10/2003 |
| WO | WO 98/37928 | 9/1998 |
| WO | WO 00/32270 | 6/2000 |

* cited by examiner

*Primary Examiner*—Brij Shrivastav
*Assistant Examiner*—Tiffany A Fetzner
(74) *Attorney, Agent, or Firm*—James Creighton Wray; Clifford D. Hyra

(57) ABSTRACT

Diagnostic and Therapy apparatus and methods use non-ionizing radiations which are based on integration of nuclear magnetic resonance and radiation manipulation. Quantitative diagnostics integrate the following devices: manual control digital filter/selector (18), frequency matrix monitor (25), frequency image monitor (26), and control panel (28). Therapy integrates the following devices: resonating antenna for radio frequency (4), low radio frequency signal processor/modulator (10), radio frequency pulse amplifier (13) and central pulse control (16). Internal parameters of the emission, such as frequency, power and polarity are selectively manipulated to personalize the therapy and to significantly improve the levels of selectivity and/or differentiation of all the processes.

9 Claims, 11 Drawing Sheets

Figure 1:
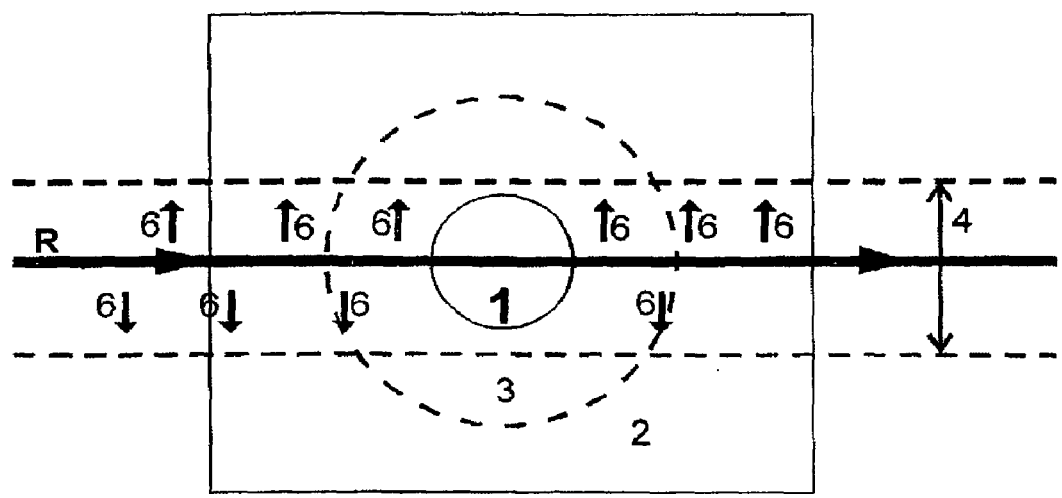
Figure 2A:
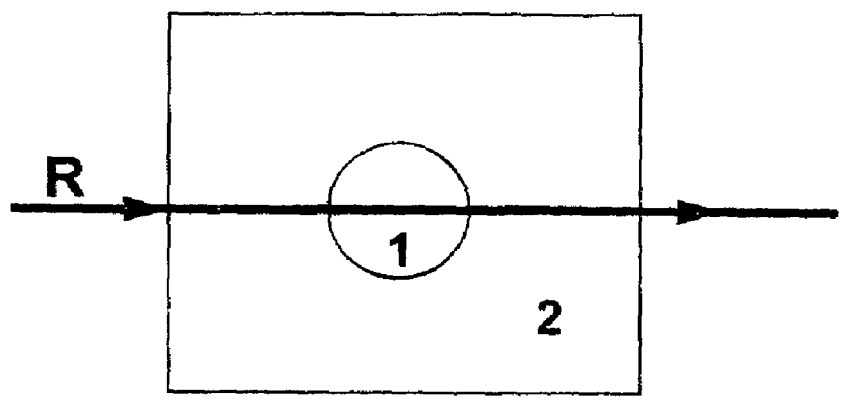
Figure 2B:
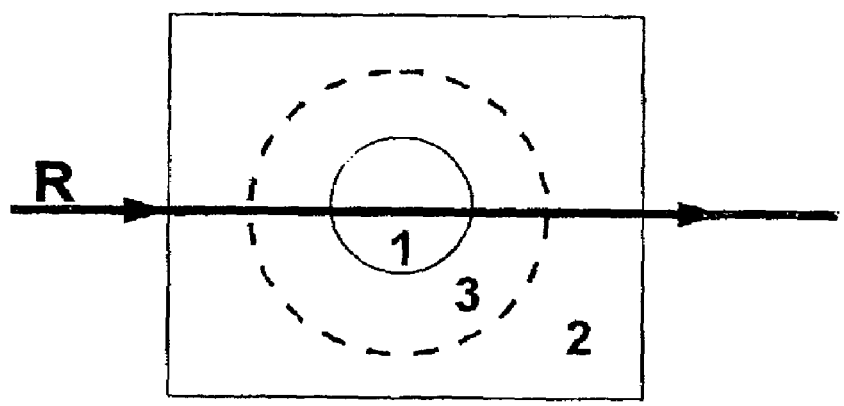
Figure 3:
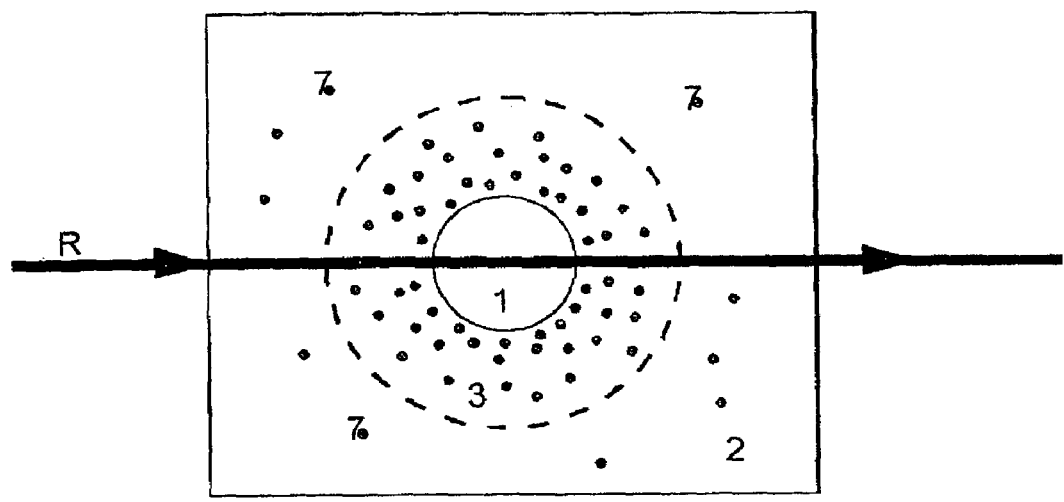
Figure 4:
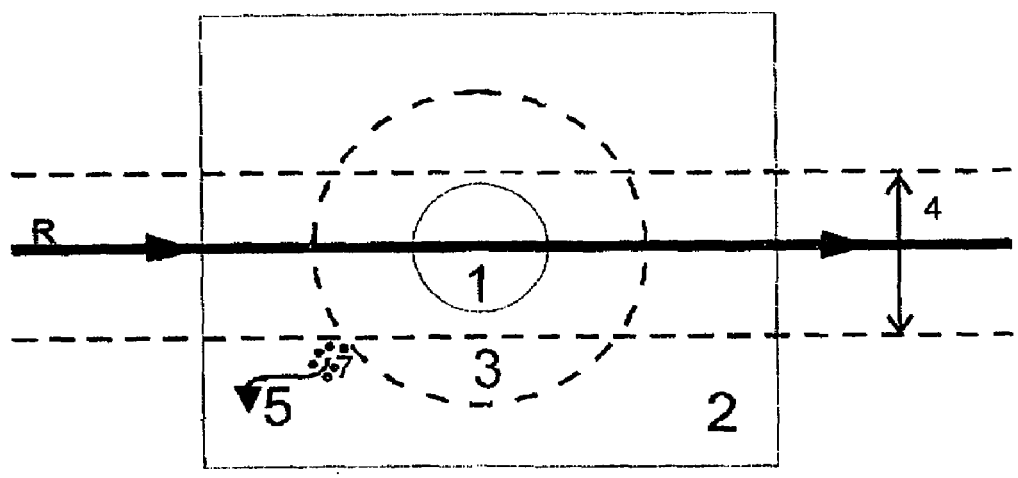
Figure 5:
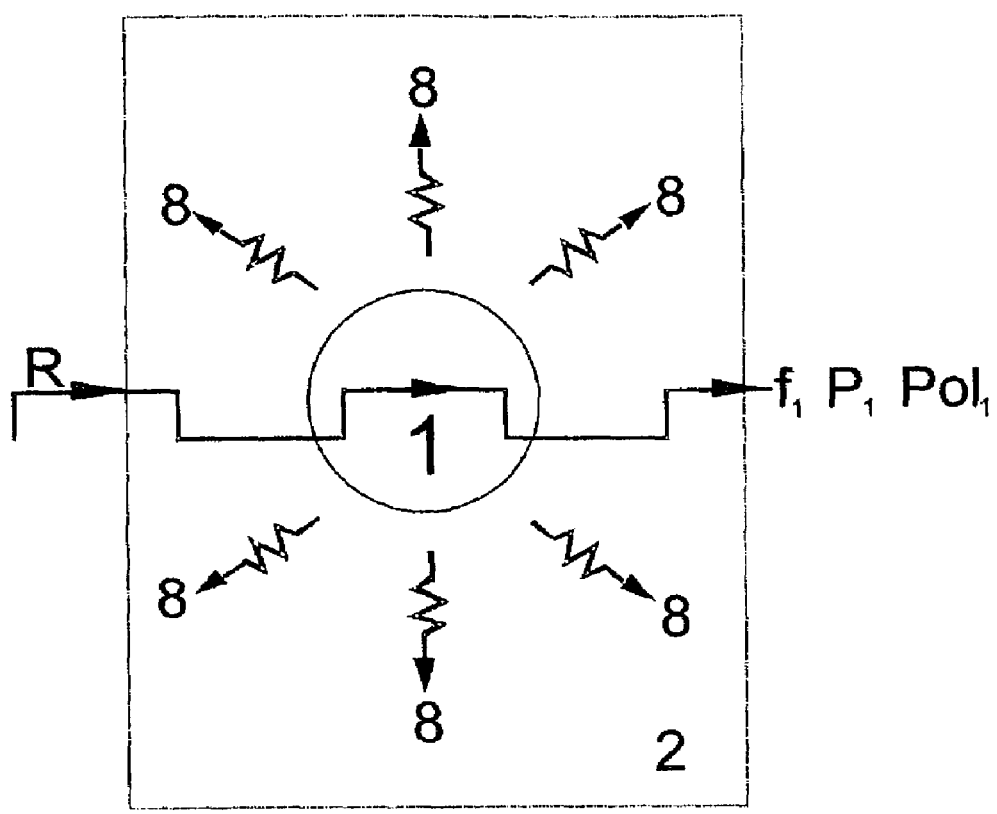
Figure 6:
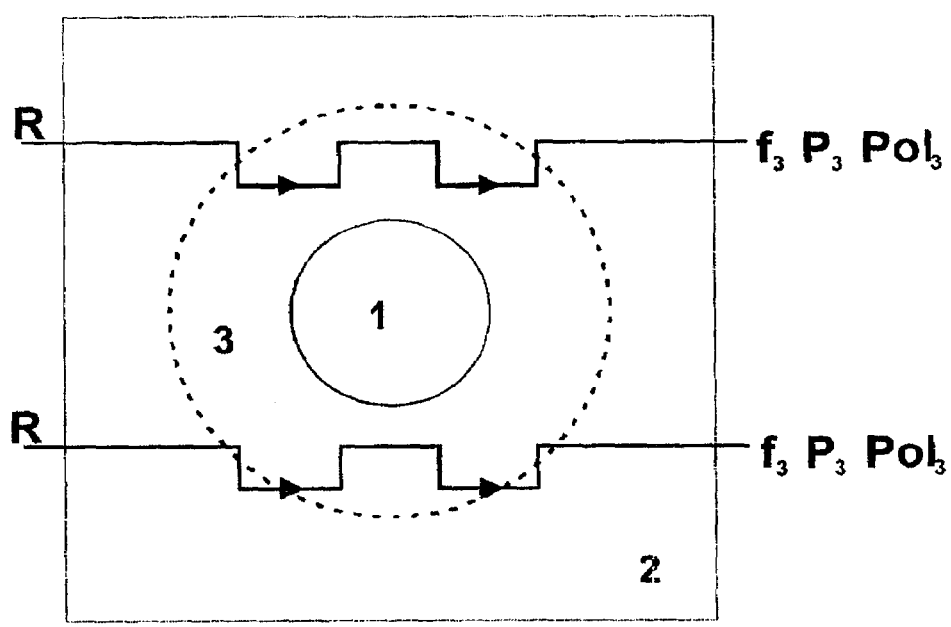
Figure 7:
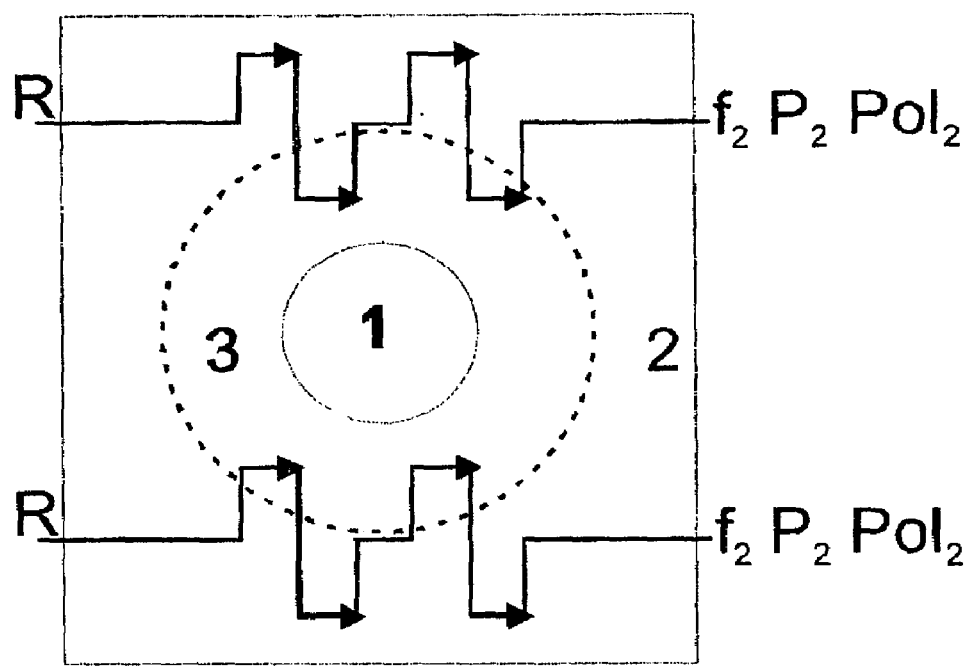
Figure 8:
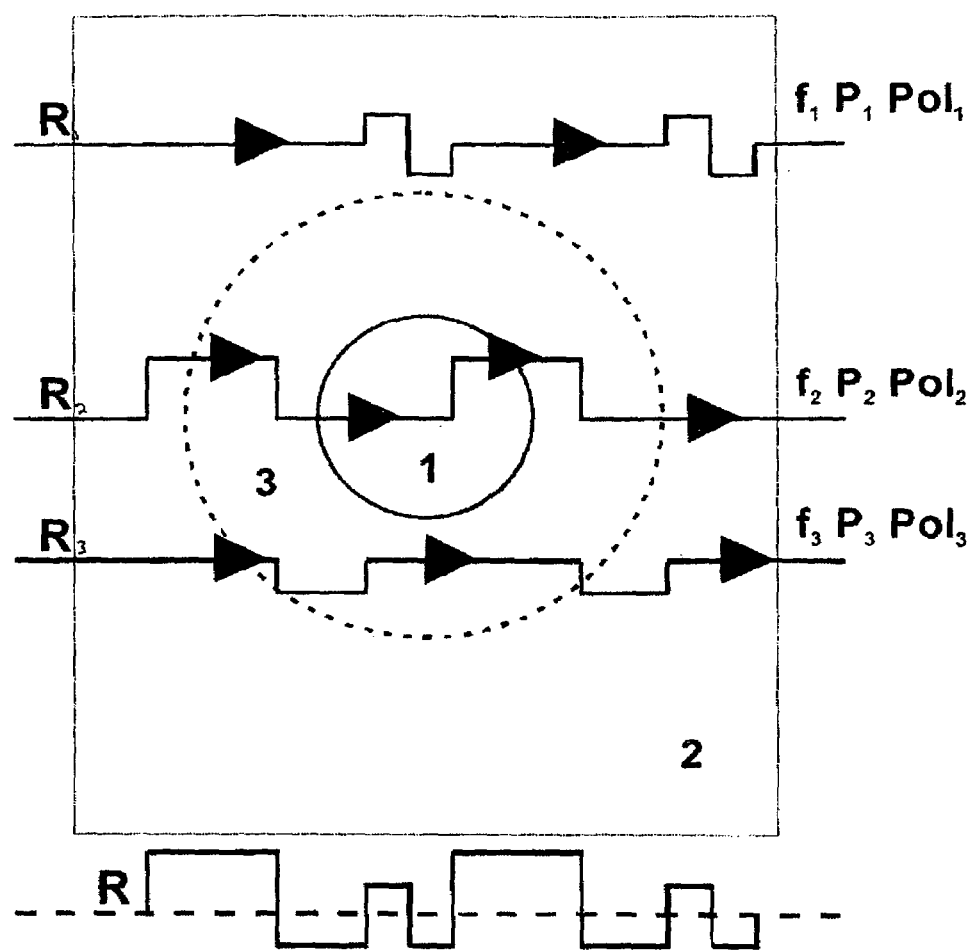
Figure 9:
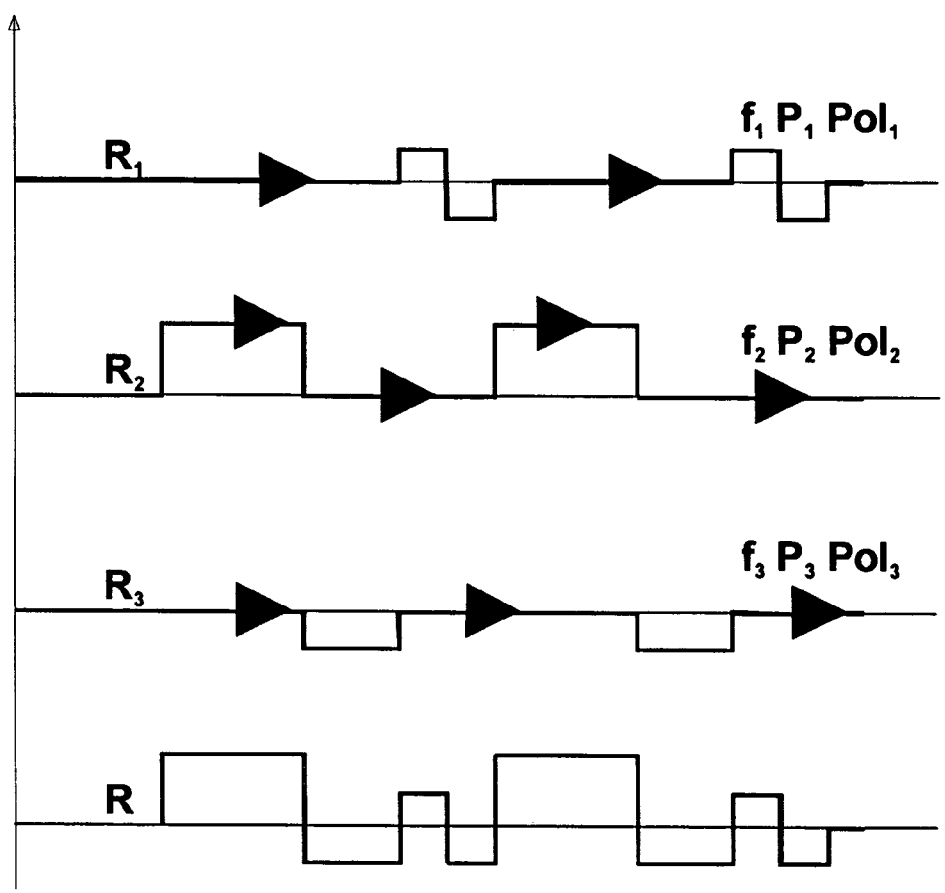
Figure 10:
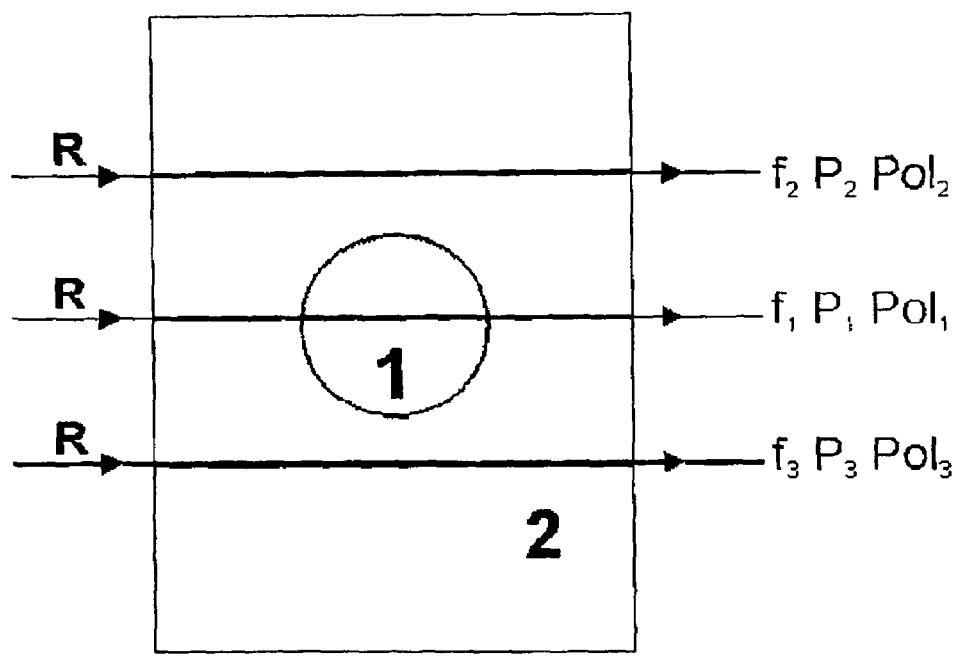

APPARATUS AND ASSOCIATED METHOD THAT INTEGRATE THE MODALITIES OF DIAGNOSIS AND THERAPY TO TREAT, IN PRINCIPLE, PATHOLOGIES GENERICALLY IDENTIFIED AS CANCER AND HIV/AIDS

This application claims the benefit of PCT/MX2003/000105 filed Nov. 28, 2003, which is hereby incorporated by reference in its entirety.

FIELD OF THE INVENTION

This Invention refers to the VPEPN/H-201 "Zero Series Prototype" Apparatus and associated Method that allow to Quantify the Diagnosis and to Selectively manipulate parameters of the Non-ionizing electromagnetic emission, such as: Frequency, Power and Polarity, with the objective of using the aforementioned emission as a Personalized Therapy, to treat, in principle, pathologies generically identified as Cancer and HIV/AIDS. Meaning that the Apparatus integrates in itself the modalities of Diagnosis and Therapy, uses exclusively Non-ionizing electromagnetic radiation and is based theoretically and functionally on the Physical Principle of Resonance and in particular on the principle known as Nuclear Magnetic Resonance (NMR), contributing the following important innovative elements: the Quantification of the Diagnosis and the Selective Manipulation of some of the parameters that intrinsically form part of the electromagnetic emissions of subject, and that, we reiterate, for the modality of personalized therapy specifically.

We want to make known as a special explanation, that the aforementioned VPEPN/H-201 Apparatus, represents what would be a "Zero Series Prototype" of a Nuclear Magnetic Resonance (NMR) Apparatus of imprecise origin (manufacturer) which, assigned to the conceptual and functional benefits of this invention, is able to operate as required, in the modalities identified as Quantitative Diagnosis and Personalized Therapy.

That the manufacturers can implement the Invention in the production lines in use, generating as a consequence, new Apparatuses with this innovative functional duality of Quantitative Diagnosis and Personalized Therapy, that has been improved, in addition; but the Invention can also be implemented, to the compatible technological methods in use, whether adding the option of Quantitative Diagnosis only, or adding to the previous one, the Personalized Therapy proposed in the Invention.

BACKGROUND OF THE INVENTION

In the process of mummification, the Egyptians used, perhaps empirically, a combination of Complementary Radiations and Chemical Compounds to make the preservation of bodies more effective; in the 18th century, around 1774, the German Professor, Franz Anton Mesmer (1734-1815), developed his own theory that generated a current of followers of what was known at the time as "Mesmerism", using Magnetism as a Therapeutic Method for different types of pathologies; by 1845, Michael Faraday (England), researched the Magnetic Properties of dry blood; by 1897, the physicist J. J. Thomson, of Cambridge University (England), discovered the Electron. During the following two decades a series of outstanding physicists among which Max Planck, Ernest Rutherford, Niels Böhr, Erwin Schrodinger and Werner Heisenberg are included, based their research on the work of each other to advance in the study of the structure and properties of the Atom and the Atomic Particles, with this, they revolutionized Physics and elaborated a new theory and language known as Quantum Mechanics; in the early $20^{th}$ century, the Russian Engineer George Lahkhovsky, used Non-Ionizing Electromagnetic radiations without Complementary Substances, in order to treat different types of Tumors; in 1936 Linus Pauling and Charles D. Coryell discovered that the Magnetic State of hemoglobin changed depending on its state of oxigenation; in 1937 Isidor Isaac Rabi and his colleagues developed the Molecular Beam Magnetic Resonance by passing a beam of lithium chloride molecules through a Magnetic field and then subjecting it to Radio waves; in 1945 and only three weeks apart, the research groups directed by Edward Purcell and Felix Bloch independently proved the phenomenon known as "Nuclear Magnetic Resonance of Condensed Matter"; in 1948 Nicolaas Bloembergen, Edward Purcell and Robert Pound published a paper on "Nuclear Magnetic Relaxation"; in 1949 Erwin Hahn discovered the Spin Echo Phenomenon in the measurements of Nuclear Magnetic Resonance (NMR); in the late 1950's, Russell Varian, of Varian Associates, proposed a new Impulse Method called Nuclear Magnetic Resonance (NMR) with Fourier Transform. Practically at the same time, Irving Lowe and Richard Norberg, both from the University of Washington in Saint Louis, theoretically and experimentally demonstrated how to obtain all the available results of the experiments with Continuous Wave through the Mathematical Manipulation of the Signals produced in an experiment with Impulses. However, at that moment this Mathematical Process necessary to analyze the data of the Impulses (a technique called Fourier Transformation) was not practical (Viable) due to the limitations of the computer equipment of the time; in the 1960's Richard Ernst and Weston Anderson applied the Fourier Analysis to the Impulse Signals to increase the sensitivity of Nuclear Magnetic Resonance; in the second half of the $20^{th}$ century, Antoine Priore, an Italian electronic technician, developed a therapeutic proposal using Non-Ionizing Electromagnetic Radiation without using Complementary Substances to treat different types of Tumors; in 1969 Raymond Damadian, a physician at the Medical Downstate Center of Brooklyn (N.Y.), began to devise the way of using this technique to detect the first signs of Cancer in the body. In an experiment made in 1970, he extirpated a series of fast growing Tumors that had been implanted in laboratory rats and proved that the Nuclear Magnetic Resonance (NMR) of the Tumors was different to NMRs of normal tissue. In 1971 he published the results of his experiments in "Science" magazine although the Clinical Reliability of his Method had not yet been proved for the Detection or Diagnosis of Cancer; in 1971 Godfrey Hounsfield built the first Computerized Tomography Scanner, which is the base of almost all the imaging systems used nowadays; in 1972 Paul Lauterbur combined the idea of the Gradient with the one of the Computerized Tomography Scanner to make several projections and to reconstruct them to obtain the first Magnetic Resonance image (MRI); in 1976 Peter Mansfield conceived the Echoplanar Technique, which can explore all the brain in a few seconds and in the same year he and his English colleagues, published the first image of a human finger obtained by Magnetic Resonance (MR); in the 1980's Russian Scientists used the combination of Non-Ionizing Electromagnetic radiations with Complementary Substances denominated "Target" Substances as a Therapy against Tumors; in 1990 Seiji Ogawa detected variations in the oxigenation of the local tissue using contrast media that depended on the oxygen level of blood; in the 1990's German Scientists developed the Proposal of the Russian Academicians, using "Nano-particles" as "Target" Substances in combination with Non-Ionizing electromagnetic radiations to treat different types of Tumors; by the late of 1990's Professor Panos Pappas (Greece) presented a therapeutic proposal denominated "PAPIMI" in which he used Non-Ionizing Electromagnetic Radiations without using Complementary Substances to treat different types of Tumors; in 1992 John W.

Belliveau, Peter Bandettini and Seiji Ogawa independently published their studies on the cerebral answer to sensorial stimulation, for which images obtained by Magnetic Functional Resonance (MFR) were used and in October, 2003 Paul Lauterbur (American) and Peter Mansfield (British) were awarded the Nobel prize in Medicine for their fundamental discoveries related to the use of Nuclear Magnetic Resonance (NMR), which lead to the development of a modem system that produces three-dimensional images of the organs inside the human body.

In the state of the technique, there are several Apparatuses and/or Methods for the Diagnosis and Therapy of both Cancer and HIV/AIDS. In the case of Cancer, there are problems of Empiricism associated to the Diagnosis. The Apparatuses and Methods associated to the Diagnosis of Cancer through Images, only provide a "mute" Image of the pathology object of study; i. e., they provide a Qualitative Diagnosis, that does not express anything specifically, thus the level of Empiricism in the clinical interpretation of the images obtained continues and through Biopsies can a Diagnosis with a high index of certainty be obtained. For HIV/AIDS we consider that the available options of Diagnosis in use at the moment are adequate and reliable.

In the field of Cancer Therapy, there are different approaches such as Chemotherapy that uses chemical compounds generically identified as Cytostatic and Non-Cytostatisc drugs, Radiotherapy that uses Ionizing radiations in more than 90% of the therapeutic applications and, in the field of No-Ionizing radiations, that area of research is practically and mainly in an experimental phase; in both cases (Ionizing and No-Ionizing radiations) the levels of Selectivity and/or Differentiation are practically null, thus, the index of Empiricim is high.

For Patentability effects, the Registration of the Linear Particle Accelerator—an apparatus whose fundamental contribution is to eliminate certain limitations of the radiations used in "Conventional Radiotherapy" (with Ionizing Electromagnetic radiation), such as: low propagation speed, insignificant penetrability, etc.—was accepted by all the International Scientific Community and by institutions such as the World Intellectual Property Organization (WIPO).

The aforementioned apparatus and its associated method "somehow" manipulates the above mentioned Ionizing radiation, but only at the level of the total amount of radiations that form part of the emission as a whole the emission in a given moment, but NOT in a Selective and separate way, which is the particular and distinctive case of this Invention.

Our Scientific and Technical proposal in the sense Selectively manipulating the parameters that conform the electromagnetic emissions of therapeutic interest such as Frequency, Power and Polarity, is without doubt of a greater Conceptual and Practical scope and it is duly guaranteed with the Prospective Integral Functional Profile that our proposal unobjectionably has in opposition of other Magnetic Resonance Systems and/or Apparatuses not related to the medical profile and the indistinct and/or respective Methods associated to the same.

Surgery is another additional or complementary therapeutic option, with the well-known adverse effects surgery has in itself.

In the case of the abovementioned therapeutic options destined to Cancer, we want to make known that these options are applied separately and/or in combination, depending on each particular case, and that for the specific case of HIV/AIDS the totality of therapeutic options offered at the moment are based on Vaccine Candidates (preferably through the administration of so called Vaccine Cocktails which are deemed more effective) and other pharmacological candidates such as interferons, monoclonal antibodies, etc. that can be combined or not with vaccines, and this, in direct function of the clinical state of each particular case.

In the group of Apparatuses, patent request no. 1361418 of China, published on Jul. 31, 2002, by Qiu Jianqin and collaborators, which protects a control panel for a Nuclear Magnetic Resonance (NMR) Apparatus that operates using Radio frequencies (RF) and makes a multiple direct sampling of the Variable Frequency; the design of the U.S. Pat. No. D 457,885 S, for Matsumura Kiyoshi and collaborators, published on May 28, 2002, for an exploratory Apparatus for tomography by means of Nuclear Magnetic Resonance (NMR); another Apparatus is protected by U.S. Pat. No. 5,736,858 of the United States of America, for Katznelson and collaborators, published on Apr. 7, 1998, that deals with a complete body of gradient coils that obtains ultra-fast images; another similar patent is U.S. Pat. No. 5,530,355, for Doty and collaborators, published on Jun. 25, 1996, that protects a transversal gradient coil Apparatus that provides a Magnetic Resonance (MR) image.

For the Diagnosis, there is the use of imaging contrast agents in the state of technique, as is the case of international application WO 03013616, for Mainero Valentino and collaborators, published on Feb. 20, 2003; the United States of America patent application no. US2002121898, for Brevard Christian and collaborators, published on Sep. 5, 2002, contains an excitation circuit and a test that measures and recovers the return signal emitted by the Nuclear Magnetic Resonance (NMR) Apparatus; U.S. Pat. No. 5,590,656 of the United States of America, for O'Dorisio and collaborators, published on Jan. 7, 1997, describes and protects the use of radio tracers as markers of the tissues of pathologies, this Method includes the administration of a radio tracer and also a test of radiation detection; U.S. Pat. No. 5,596,992 of the United States of America, for Haaland and collaborators, published on Jan. 28, 1997, covers the classification of cancerous tissue by infrared radiation; U.S. Pat. No. 5,579,773 of the United States of America, for Vo-Dinh and collaborators deals with an Apparatus and Method for the Diagnosis of Cancer using a laser; U.S. Pat. Nos. 5,420,510, 5,404,882 and 5,281,917 of the United States of America, and European patent EP 0234524, talk about Methods that use images to diagnose Cancer.

For the Diagnosis of pathologies like Cancer, there are documents in the state of the technique or state of the art that report the use of the Apparatus and Method to improve the Diagnosis of Cancer; for example, the patent of the U.S. Pat. No. 6,535,755, for Ehnholm, published on Mar. 18, 2003, that protects the Apparatus and Method to increase the signal/noise ratio of a Nuclear Magnetic Resonance (NMR) signal, with which the temperature of the operation of the treatment of Cancer is controlled; patent of the U.S. Pat. No. 5,885,547, for Gray and collaborators, published on Mar. 23, 1999, describes a Cancer Therapy that uses internal radionuclides that emit beta and gamma radiation; patent of the U.S. Pat. No. 5,596,619 for Carol, published on Jan. 21, 1997, describes an Apparatus and Method for a Therapy using a spatially modulated beam that crosses the tumor; international application WO 9620733, for Freytag Svend and collaborators, published on Jul. 11, 1996 describes a Cancer Therapy that uses selective markers that are exposed to radiation, obtaining in this way a combined Method; patent of the U.S. Pat. No. 5,528,652, for Smith and collaborators, published on Jun. 18, 1996, describes a Cerebral Therapy Method, using Ionizing radiation; application for international patent WO 9412240, for Laustsen Torben and collaborators, published on Jun. 9, 1994, refers to a Cancer Therapy that uses infrared radiation with optical fibers; European patent EP 0562644, for Nunan Craig and irregular radiation in which the Power of the incident Ionizing radiation is adjusted;

patent of the U.S. Pat. No. 5,231,984, for Santana-Blank, published on Aug. 13, 1993, describes an Apparatus and Method to perform a Laser Therapy on cancerous tissues of the skin; European patent EP 0406454, for Albini Domenico and collaborators, published on Jan. 9, 1991, refers to an Apparatus that performs photochemistry with the aid of a laser; U.S. Pat. Nos. 4,815,448 and 4,815,447, for Mills, published on Mar. 28, 1989, protect a Therapy that uses Selective radiation of Frequencies combined with agents used in Chemotherapy; U.S. Pat. No. 4,690,130, for Mirell Stuart, published on Sep. 1, 1987, protects an electromagnetic control system for Chemotherapy; Japanese patent JP 57185220, for Endou Hiroshi and collaborators, published on Nov. 15, 1982, proposes a Therapy of radiation with visible light with the aid of an agent that contains an active component and a chlorophill derivate.

During Ionizing or Non-Ionizing Therapy (and only when the Resonance is obtained), an region of Hyperthermia in the area surrounding the radiated pathology appears; thus, Hyperthermia is a problem associated to all radiation Therapies used nowadays; however, there are documents, in the state of the technique or in the state of the art, that refer to the problem, for example, payents of the U.S. Pat. No. 5,441,532 and 5,251,645 for Fenn, published on Aug. 15, 1995 and Oct. 12, 1993, respectively, protect an assembly of elements in phase with the incident Radiofrequency that causes the heating, the Power of the incident radiation is controlled to avoid excessive heating where it is not needed; U.S. Pat. No. 4,819,642 patent for Ndersen and collaborators, published on Apr. 11, 1989 does the same; as well as U.S. Pat. No. 4,702,262 patent for the same inventor, published on Oct. 27, 1987, in which they basically locate the Hyperthermia area.

We can additionally refer as patents of reference of interest, to the following: EPO U.S. Pat. Nos. 5,690,109 A, WO 91/07132 A, EP 0695560, WO 9519841, EP 0198257, WO 8804414, EP 0252118, and WO 8703798; from Spain patents No. 0240990, 0305008, 0284542, 0355750, 0340005, 0705603, 0400940, 0512981, 0650601, and 0711121; from Switzerland patents No. CH 681356 and CH 669733; from Australia patents No. 563137, 528476 y 534533; from Japan patents No. 04102465 and from the U.S. Pat. Nos. 4515165, 4524779, 4691712, 4935631, 5079698, 5168514, 5442675, 5464445 and 5609816.

In all the therapeutic options based on Ionizing and Non-Ionizing radiations currently in use, the radiation parameters are not Selectively manipulated with the purpose of responding to determined specific requirements that the therapeutic interests, the Bio-Energetic Balance, and/or the particular clinical state of the patient at a determined time may require, due to the existing Conceptual Limitations and current state-of-the-art; in our Scientific proposal we do Selectively and Indistinctly manipulate parameters such as Frequency, Power, and Polarity of Radiation, since they are essential to adequately guarantee the resolution of conceptual, functional and technological limitations, among others, such as the ones mentioned before".

Furthermore, it is very important, to duly recognize the Viability of this Invention for the following reasons:
 a) In the Scientific order because all the Principles of Work that support it are perfectly demonstrable at theoretical level.
 b) In the Technical order because we have necessary and sufficient means to integrally implements it in the practical order.
 c) In the Commercial order because the Demand is adequately identified, for an Offer of the scope and making as the one that is the subject of this Invention.

The Innovative Functional Profiles exposed above can only be made real through the VPEPN/H-201 "Zero Series Prototype" Apparatus and its associated Method, which we mention as an example, thanks to the integral conception of our Scientific-Technical Proposal in the Conceptual and Functional orders.

BRIEF DESCRIPTION OF THE INVENTION

An objective of this Invention is the exclusive use of Non-Ionizing Electromagnetic Radiation to which parameters such as Frequency, Power and Polarity are selectively manipulated, and the latter, exclusively for the (Personalized) Therapy Modality that shall be applied, in principle, to pathologies such as Cancer and HIV/AIDS.

It is another objective of the present Invention, to eliminate the level of Empiricism that today distinguishes the Diagnosis and Therapy Modalities, since exact indexes of Selectivity and/or Differentiation are obtained when the Resonance Frequency is quantified for the first time and therefore, the Diagnosis of the Pathology. This achievement unequivocally conditions the ability to knowledgably apply a Personalized Therapy with a scope and making that has no precedents in the medical practice.

It is still another objective of this Invention, to eliminate the harmful effects Hyperthermia causes in healthy tissue and other tissues that surround the pathology treated with Electromagnetic radiations, whether they are Ionizing or Non-Ionizing.

It is yet another objective of this Invention to totally avoid the use of the so-called "Target" Substances, avoiding the problems associated to the possible Evacuation of these substances.

It is also an objective of this Invention to totally eliminate the use of Ionizing radiation both for Diagnosis as well as for Theray Modalities.

It is an objective of this Invention to avoid the collateral damage caused by Chemotherapy and/or Radiotherapy to the, Nervous and Immune Systems.

It is another objective of the Invention to decrease the use of Surgery as a therapeutic option.

It is also an objective of this Invention to decrease the time that passes between Diagnosis, Therapy and Rehabilitation of the patient.

It is also an objective of this Invention to provide an Apparatus and associated Method that can be quickly implemented in the so-called Health Market.

It is also an objective of this Invention to decrease the high Costs specifically associated to Research and Development "R&D" related to the search of therapeutic options for pathologies like Cancer and HIV/AIDS, among others.

It is another objective of the Invention, to provide a Personalized Therapy for the pathologies generically identified as Cancer and HIV/AIDS, among others.

It is also an objective of the this Invention to definitively annul the harmful effects and consequences that cause Cellular Mutation and overlap, Biological conducts that distinguish, as if they were "Biological Standards", pathologies such as Cancer and HIV/AIDS, among many others.

BRIEF DESCRIPTION OF THE ILLUSTRATIONS

With the purpose of promoting the understanding of the Theoretical and Scientific-Technical Principles of the Invention, we will now refer to the modalities shown in the illustrations and a specific language will be used to describe them. However, it shall be understood that it is not our intention to limit in Any way the scope of the Invention, any alteration and modification of the VPEPN/H-201 "Zero Series Prototype" Apparatus and its associated Method, as well as other Systems and/or Devices that use the Physical Principle of Resonance in profiles of use or application different to the ones described in this Invention shall have to be considered to be under the protection of the scope and spirit of this proposal; thus, this very special mention is made with the express intention of making it clear that in this application we have followed the preferred modality to illustratively and decriptively exemplify the application of the Invention of subject. That said other applications made under the Work, Manufacture and Integral Conception Principles of our Scientific-Technical Proposal (of the Principles of the Invention) are illustrated in the Proposal and are completed and exposed in the same way as would normally be, so that someone skilled in the art to which this Invention refers may reproduce them, as well as by specialists of any other potential application profiles different to the subject Investigation as already described.

FIG. 1

Ionizing Radiations

It can be seen that in the area of influence of the path (4) of Radiation (R), the Radiation Ionizes (6) the matter it crosses (2), be this Biological or not, aside from generating harmful side effects in the Area Surrounding the Pathology (1) as a product of Hyperthermia (3).

FIG. 2

Non-Ionizing Radation WITHOUT "Target" Substance

In this illustration it can be seen the two possible behaviors that can take place:

2a) WITHOUT Hyperhermia, in case there is NO hyperthermia caused by Radiation (R), not in Resonance with the Pathology of reference (1) in all the matter it crosses (2).

2b) In the Surrounding Area WITH Hyperthermia (3), if the Radiation (R)

Resonates with the Pathology (1) then there is Resonance and the harmful side effect caused by Hyperthermia can be seen on the surrounding Healthy Biological tissue (2).

FIG. 3

Non-Ionizing Radiations WITH "Target" Substance

Hyperthermia (3) caused by Radiation (R) can be seen in the area surrounding the Pathology (1), this Hyeprthermia causes harmful side effects aside from the problem of Evacuating the Target Substance (7) used from the healthy tissue (2).

FIG. 4

Areas of "Conflict"

Area affected by the Pathology (1), healty Surrounding Area, (2) Healty Surrounding Area affected by Hyperthermia (3), Tissue and area possibly affected by Radiation (R) in the Area of influence (4). The potential Evacuation (5) of the "Target" Substance (7) is visualized.

FIG. 5

Pathologic Area

The Pathologic Area (1) is represented being crossed by the Non-Ionizing Electromagnetic radiation (R) with a Resonance Frequency ($f_1$) and the respective and necessary Power value ($P_1$) that will destroy it. In this case a Thermal Dissipation (8) (irradiation) is generated in the Healty Surrounding Area (2) produced by Hyperthermia. In this hypothetical case a Positive Polarity ($Pol_1$) is assumed as an indication of Energy Contribution.

FIG. 6

Surrounding Area of Healthy Tissue with Hyperthermia

It represents the Healty Surrounding Area (2) affected by Hyperthermia (3) being passed through by the Non-Ionizing Electromagnetic Radation (R) in the Resonance Frequency ($f_3$) and its respective Power value ($P_3$) that shall evacuate the Excess Heat yielded by the Pathological Area (1). In this hypothetical case a Negative Polarity ($Pol_3$) is assumed as an indication of Energy Absorption.

FIG. 7

Healthy Tissie Perimetral Zone

The Pathology (1) is represented and the Healthy Surrounding Area (2) not affected by Hyperthermia (3) being crossed by the Non-Ionizing Electromagnetic Radiation (R) in the Resonance Frequency ($f_2$) and its respective and necessary Power value ($P_2$) and Alternate Polarity ($Pol_2$) (in this hypothetical case), which shall Contribute or Yield Energy to this area (2) and this, in direct function with the Therapeutic interests and/or the Bioenergetic Balance.

FIG. 8

Integration of the Emissions

It is the visual integration of ILLUSTRATIONS 5, 6 and 7 in order to have an approximate idea of the concept of "Sequence of Emission Pattern", in this specific hypothetical case; where $R_1$ is the Radiation that acts on the healthy tissue (2), $R_2$ is the Radiation that acts on the Pathology (1) and $R_3$ is the Radiation that solves the problem of Hyperthemia (3). The R-3 Complex Therapy Modality, operates on three different frequencies integrated in the chart of Radiation (R), and this is what better illustrates the Main or Basic Concept of the Scientific Proposal.

Where the behavior or ratio in values of the Frequency (f) and Power (p) Variables would be:

$f_1 \neq f_2 = f_3$
$P_1 > P_2 = P_3$
Polarity (Pol), where: $Pol_1$ is positive (+)
$Pol_2$ can be positive (+) or negative (−)
$Pol_3$ is negative (−)

FIG. 9

Hypothetical Charts of the Main or Basic Principle of the Integral Operation of the Apparatus; in this particular case, for the of R-3 Complex Therapy Modality Where $R_1$ is the Radiation that acts on the healthy tissue, $R_2$ is the Radiation that acts on the Patology and $R_3$ is the Radiation that solves the problem of Hyperthermia and the behavior or ratio in values of Frequency (f) and Power (p) Variables would be:

$f_1 \neq f_2 = f_3$
$P_1 > P_2 = P_3$
Polarity (Pol), where: $Pol_1$ is positive (+)
$Pol_2$ can be positive (+) or negative (−)
$Pol_3$ is negative (−)

FIG. 10

"Conventional" Hypothetical Emission

It represents an Emission of Conventional Radiofrequency that passes through Biological Substances (2) and some of the parameters that compose it, such as Frequency, Power and Polarity, are shown since they were considered of high-priority in our studies and analysis. The Radiations $R_1$, $R_2$ and $R_3$ form a beam that cannot be functionally divisible and in this example the ratio between the fundamental parameters is:

$f_1 \neq f_2 \neq f_3$
$P_1 = P_2 = P_3$
$Pol_1 = Pol_2 = Pol_3$ (Indeterminate for this example)

FIG. 11

Simplified Functional Scheme of the VPEPN/H-201 "Zero Series Prototype" Apparatus In this illustration the fundamental Devices and/or Technologic Parts that make this Invention Viable are shown conceptually and Functionally integrated:

a) Radiofrequency Resonating Antenna (4)
b) Low-Signal Radiofrequency Processor/Modulator (10)
c) Radiofrequency Pulse Amplifier (13)
d) Manual Control Digital Filter/Selector (18)

e) Central Pulse Control (16)
f) Frequency Matrix Monitor (25)
g) Frequency Image Monitor (26)
h) Control Panel (28)

It is important to note that without the Conceptual and Functional integration of the abovementioned Devices and/or Parts (Technological Innovations) it would not be possible to attain the objectives and goals achieved with this Invention.

That the Devices and/or Parts listed in paragraphs (d, f, g, h) are essential to operate the Apparatus in the Quantitative Diagnosis Modality, and that to operate the Apparatus in the Personalized Therapy Modality the former plus the ones listed in paragraphs (a, b, c, e) would be essential.

DETAILED DESCRIPTION OF THE INVENTION

This Invention is represented to "exemplify", through the VPEPN/H-201 "Zero Series Prototype" Apparatus and associated Method which allows to Selectively manipulate parameters such as Frequency, Power and Polarity of the radiation that will be used as a Therapy and that will affect an area previously identified and localized as an area of Threapeutic interest; the Apparatus aside from Quantifying the Resonance Frequency of different cellular compositions, shall then guarrantee a Quantitative Diagnostic which undeniably conditions the application of a Personalized Therapy that has no precedents in the medical practice, as well as significatively improving Diagnosis as an independent modality.

The procedure begins by using the technique traditionally known as Nuclear Magentic Resonance (NMR) in use at present, obtaining in this way an image of the area affected by the pathology (Qualitative Diagnosis), once the image generated by the area studied is obtained in its phase of return to equilibrium and having established with it the adequate interconnection to the Frequency Processor (17) of Illustration 11, the Frequency Matrix Monitor (25) that provides reliable and exact information of the specific values of the Resonance Frequencies localized in the different areas studied, in this Monitor, we can accurately see the specific values of the Resonance Frequencies, the Frequency Image Monitor (26) with which the images are obtained in function of the specific net Frequency of each tissue, organ and or system being studied, we shall then get with the aforementioned device, and only at that moment, a graphic Profile of the Frequencies of the studied area, aside from the traditional "mute" images that can be obtained to (Qualitatively) Diagnose due to the limited options given by the state of the technique or the state of the art at this time.

The Conventional Image Monitor (24) only provides information at a Qualitative level, which implies an Empirical Diagnosis, but this is also a valuable information that provides images that are a direct function of the density of tissues that would be integrated to the other previously mentioned data (visual and value graphs).

From the previous, we can infer that the information obtained is an Electromagnetic Profile of Resonance Frequencies that provides accurate information both for Diagnosis and for Therapy, this procedure which favors the present medical practice for treating pathologies generically identified as Cancer and HIV/AIDS, in principle.

A Modality of Quantitative Diagnosis is proposed, since using the Frequency Matrix Monitor (25) the Specific, Particular and Respective Values of the Resonance Frequencies of the areas of interest are accurately known and the Frequency Image Monitor (26) provides images that are in direct function of the aforementioned Frequencies which provide a graphic, and visual profile of the Frequencies of the studied area and through the Conventional Image Monitor (24), images that are in direct function with the density of the tissues are provided, then under the terms and conditions mentioned before, an Electromagnetic Profile of Integral Resonance Frequencies that conditions the accurate and effective application in sequence of Diagnosis and Therapy, and in this way, a Personalized Therapy that has no precedents in today's medical practice can be implemented.

With the Control Panel (28) located in the Operator's Console (22) the Manual Control Digital Filter/Selector is manipulated (18) to make a step by step scanning and analysis depending on the therapeutic requirements of the studied area, to accurately determine and define the Useful Work Resonance Frequencies (UWRF) and their respective Power and Polarity values, being the aforementioned parameters essential for obtaining first the Quantitative Diagnosis, and second to guarantee the later application of the aforementioned Personalized Therapy, as established by the Methodology proposed in the Invention.

Figure 11:
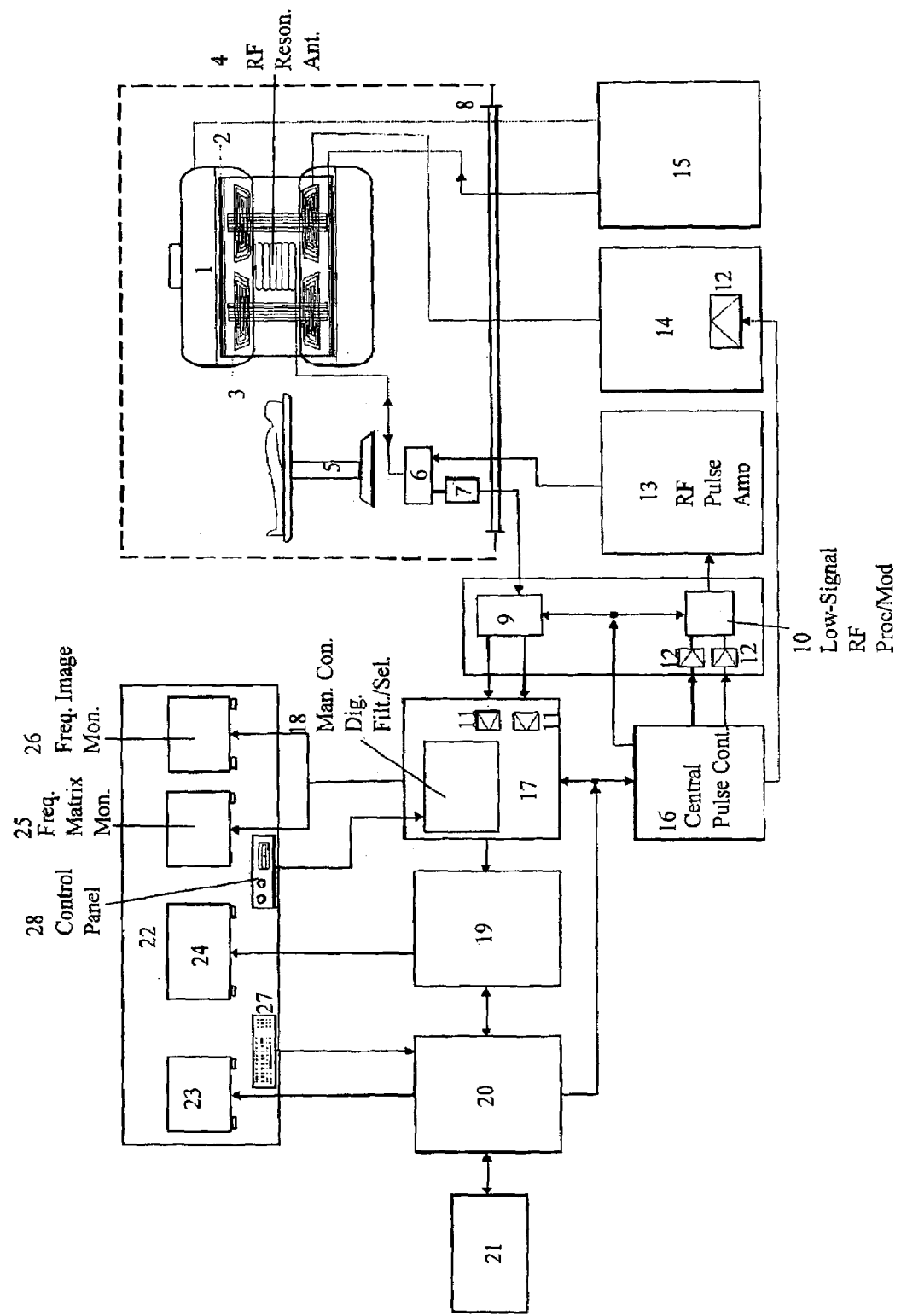

The above mentioned parameters (Frequency, Power and Polarity), already selected and modified; i.e. Selectively manipulated in function of the therapeutic interests, are programmed in the Central Computer (20) (FIG. 11) with the aid of the Keyboard (27) located in the Operator's Console (22), to give the precise instructions to the Central Computer (20) which will send the information to the Central Pulse Control (16) to be analogically processed by the Low Radiofrequency Signal Processor/Modulator (10) and amplified in the Radiofrequency Pulse Amplifier (13).

The Central Computer (20), the Central Pulse Control (16), the Digital-Analogical Converters (12), the Low Radiofrequency Signal Processor/Modulator (10), the Radiofrequency Pulse Amplifier (13) and the Radiofrequency Resonating Antenna (4), must be in operation and must have the necessary and sufficient Functional Capacity (Operational) to then handle the "New Personalized Parameters" (modified, previous Selective Manipulation) of Frequency, Polarity and, very specially, Power to next proceed to perform a new of Radiofrequency emission with the aforementioned parameters emitted with the specific objective of using them as a Personalized Therapy. As shown in the disposition of the elements in Illustration 11, the Conventional Image Monitor (24), the Frequency Matrix Monitor (25) and the Frequency Image Monitor (26) help the operator see the evolution of the treatment in the area object of Therapy.

Once this step is finished, a second Diagnosis is made using the aforesaid traditional procedure, where the generated Radiofrequency emission would be again characterized by the fact that the parameters of the emission such as Frequency, Power and Polarity would be integrated as a whole, and exclusively circumscribed to the functional criteria and design ranges of the Apparatus object of this Invention; i. e., that the Radiofrequency emission behaves as an Indivisible and Unifunctional Electromagnetic beam, in which the parameters that form said electromagnetic beam as a whole are not partially or totally variable at any moment.

It is evident that the course of action and the specific treatment for the patient will be defined, depending on the results that shall be evaluated by specialized medical personnel.

In principle, a "re-arrangement", by means of the Non-Ionizing Electromagnetic Radiation, of the cells that were catalogued as malignant is achieved, guarranteeing the absorption and/or yield of energy by the healthy and diseased cells, following a case-specific criteria associated to the specific and particular modification of some of the work parameters that form said radiations, acquiring in this way, Specific and Selective effects on healthy or diseased cells. Beams of Non-Ionizing electromagnetic radiations with specific objectives independent from each other are used.

By maintaining this cellular "re-arrangement" and its respective level of Bioenergetic Balance, the cells catalogued as malignant cannot reach (gradually or not) the appropriate energy levels to guarrantee their existence. By maintaining their Bioenergetic Levels, the healthy cells will have the real possibility of revitalizing their functions up to certain limits and thus, they may play their specific biological role in a more efficient way, which in itself implies a recovery and therefore, the conditions for what we call cellular "re-arrangement" are established.

The basis of the Scientific-Technical proposal of this Invention is the application of the Physical Principle of Resonance and in particular the one identified as Nuclear Magnetic Resonance (NMR) by means of the VPEPN/H-201 "Zero Series Prototipe" Apparatus and associated Method since it is only under the condition of Resonance in which the transference of energy in one way or another is materialized; i. e., the yield or absorption of energy. The unequivocal difference in the values of the Resonance Frequencies is the basis for the recognition of the different molecules that form the tissues, and such is precisely the basis of Nuclear Magnetic Resonance (NMR) applied with medical purposes.

By obtaining the value of the Frequency in which the malignant cellular focus Resonates and also knowing the Resonance Frequency value of the cells of the tissue that surround it, a Dual Electromagnetic Field (R-2 Simple Therapy) is applied in principle, where a thermal contribution that destroys them shall be conditioned, modifying the values of the Power of the electromagnetic emission that affects the tissue identified as malignant above the normal limits of tolerance and for the case of the surrounding tissue, the Power is maintained in the range of values used for the Diagnosis Modality. The Modality identified as R-2 Simple Therapy is suggested to treat pathologies such as HIV/AIDS and Leukemia. R-2 Simple Therapy is shown in illustrations 5 and 7.

For the case of tumors, the R-3 type Complex Therapy is suggested, this therapy is shown in Illustration 9.

Depending on the therapeutic interests and in face of the possibility of other pathologies associated and/or concurrent to the main pathology, Therapies that may be necessary and advisable such as R-4 Therapy, R-5 Therapy, among others, can be implemented.

The evaluation and selection of the Polarity (positive or negative) of the incident radiation is very important and significant since, depending on the Polarity as well as on the interests and objectives desired with respect to the Bioenergetic Balance or Equilibrium, there may be energy absorption or yield. As mentioned before, a Selective application of radiation is needed for each kind or group of malignant cells in a specific and particular way, thus the principle of application of this Invention is the use of different beams of radiation, with precise, exact and specific sequences and doses, where each is designed and intended for a specific objective (goal), being also independent from the rest. An example is shown in Illustration 8.

The Electromagnetic Field aimed to the malignant cells, will be of a Continuous and Non-Pulsating nature; in this way, the harmful effect with a greater range is guarranteed and the cells to which it is destined have few or no possibilities of survival.

According to the technological criteria hereby proposed the viral nucleus of HIV/AIDS can be precisely and accurately entered, this nucleus is in most cases very protected; hence, until now, it has been immune to the different treatments to which it has been put through.

Illustration 1, shows the effect caused by an incident beam of Ionizing radiation of the previous technique, where it can be seen that the area of action of the Ionizing radiation affects the pathogenic tissue and in the same way the surrounding healthy tissue is affected where a harmful area of Hyperthermia is also generated around the pathology. The treatment with Ionizing radiation affects all the tissue it crosses generating harmful side effects of different range and nature.

Illustration 2a, shows the effect of a No-Ionizing radiation without "Target" Substance but it does not inhibit or affect the tumoral tissue since the Frequency of the incident radiation does not make the diseased tissue Resonate and in consequence an area of Hyperthermia is not generated around it.

In illustration 2b, the Frequency of the incident radiation interacts with the tumoral tissue, making it resonate, and as a result a surrounding area of Hyperthermia is generated with the consequent harmful side effects on the surrounding healthy tissue.

In illustration 3, another Modality of Therapy is represented where a "Target" substance is used, the harmful side effect of Hyperthermia can be seen in this illustration, with the addition of the problem of the Evacuation of the "Target" substance (represented by the dispersed spots in the healthy tissue) from the body.

In Illustration 4, shows the areas of interest in Therapy with radiation of an area affected by a tumor, where the reference (1) represents the Pathological Area; area (2) is a Healthy Tissue that is partially affected by Hyperthermia pictured inside the dotted circle (3); reference (4) indicates the route of the incident radiation in the tissue that is potentially affected by it; reference (5) represents the potential Evacuation of the denominated "Target" Substance.

In Illustration 5, represents a pathological area that is crossed by a Non-Ionizing Electromagnetic Radiation that makes the pathology resonate and absorb the necessary and sufficient amount of energy to guarantee its destruction; the Hyperthermia generated by the abovementioned concept, will be solved a posteriori. The radiation that makes the pathogenic tissue has a Frequency ($f_1$), Power ($P_1$) and Polarity ($Pol_1$). The Frequency ($f_1$) is specific for that pathogenic tissue. In this Invention said Resonance Frequency is exactly measured and once it has been identified, this Invention also provides the necessary and sufficient technological resources that allow the modification of Power and Polarity of the incident radiation at will, depending on the therapeutic interests, in such a way that it is possible to rehabilitate or destroy the area identified as pathogenic.

In illustration 6, represents the incident radiation beam in the area of Hyperthermia with Frequency (f3), Power (P3) and Polarity (Pol3); which drags the excess heat emitted by the tumoral tissue that in a way is being rehabilitated or destroyed depending on the case, and consequently cooling the surrounding area affected by Hyperthermia. In this hypothetical case a negative Polarity of the incident radiation as an indication of absorption of energy is assumed. It is clarified that the Frequency (f3) was previously identified with the technique proposed in this Invention, as well as the rest of the procedure to be applied to Selectively modify or not Power and Polarity depending on the therapeutic interests.

In addition, with the knowledge of this Invention, the Resonance Frequency of a distant healthy surrounding area that has not been affected by Hyperthermia (Ill. 7) can be identified and a Non-Ionizing Electromagnetic Radiation can be aimed, with a Resonance Frequency ($f_2$) and its respective values of Power ($P_2$) and Polarity ($Pol_2$); this radiation will emit or absorb energy to this area depending on the therapeutic requirements and/or with the purpose of maintaining the Bio-energetic Balance in this area. In this hypothetical case an alternate Polarity of the incident radiation is assumed.

It is important to note that the Sequence of the Emission Pattern of the Non-Ionizing Electromagnetic Radiation must guarantee: the harmful effect with the highest range allowed on the pathogenic tissue so that the malignant cells that compose it have slight or no possibilities of survival; that it can adequately solve the Hyperthermia problem, and avoid all types of harmful side damage on the healthy tissue surrounding the pathology object of Therapy, as well as on the Nervous and Immune Systems. Illustration 8 represents the visual integration of the beams of illlustrations 5, 6 and 7 that form a single Emission Sequence and where the behavior or ratio of the values of Frequency (f), Power (p) and Polarity (Pol) fulfill the following ratios:

$f_1 \neq f_2 = f_3$ $P_1 > P_2 = P_3$

Polarity (Pol)

$Pol_1$ is positive (+)

$Pol_2$ is positive (+) or negative (−)

$Pol_3$ is negative (−)

Illustration 9, represents the hypothetical graphs of the Basic or Main Principle of Work of this Invention, note the continuous beam emission sequence used in this particular case in the Modality of R-3 Complex Therapy where the behavior or ratio of parameters such as Frequency, Power and Polarity, fulfill the following ratios:

$f_1 \neq f_2 = f_3$ $P_1 > P_2 = P_3$

Polarity (Pol)

$Pol_1$ is positive (+)

$Pol_2$ is positive (+) or negative (−)

$Pol_3$ is negative (−)

Conventional Nuclear Magnetic Resonance equipment (NMR) emits a Radiofrequency beam in which parameters such as Frequency, Power and Polarity that compose it are constant in their respective values; i. e., the subject beam is displayed as a set of indivisible and "unifunctional" radiations as well. Illustration 10 shows three (3) beams with different frequencies but equal Power and an indeterminate Polarity of equal signs. The ratio of the parameters is as follows:

$f_1 \neq f_2 \neq f_3$ $P_{1=P2} = P_3$ $Pol_1$ Indeterminate $Pol_2$ Indeterminate $Pol_3$ Indeterminate Illustration 11, shows the Simplified Functional Diagram of the Nuclear Magnetic Resonance (NMR) system of this invention, called VPEPN/H-201 "Zero Series Prototype" Apparatus, where the List/Description of the Devices and/or Parts would be the following:

1) Magnet with incorporated cooling system and Isolation for the Assembly

2) Shim coil system

3) Gradient system coil

4) Radiofrequency resonator antenna

5) Patient table

6) Transmit—Receive Selector

7) Preamplifier

8) Radiofrequency and magnetic-proof leadthroughs

9) Radiofrequency low signal processor/Quadrature demodulator with low-pass filters 10) Radiofrequency low signal processor/Modulator 11) Analog-Digital Converter (ADC)

12) Digital-Analog Converter (DAC)

13) Radiofrequency pulse amplifier

14) Gradient amplifiers X, Y, Z with Digital-Analog Converters

15) Magnet power supply

16) Central pulse control

17) Frequency Processor

18) Manual Control Digital Filter/Selector

19) Image Processor

20) Central Computer

21) Image Storage

22) Operator's Console

23) Protocol Monitor

24) Conventional-Image Monitor

25) Frequency Matrix Monitor

26) Frequency Image Monitor

27) Keyboard

28) Control Panel.

The proposed VPEPN/H-201 "Zero Series Prototype" Apparatus works exclusively with Non-Ionizing Electromagnetic Radiations, which are selectively manipulated for their application in the Modality of Personalized Therapy only; this Therapy does not generate harmful side effects of any kind to the surrounding healthy tissues. It can be applied to the different presentations and/or manifestations of pathologies in different organs, tissues and/or systems whether in a so-called latent state or in the phase of evident clinical manifestation.

With the use of this Invention, exact indexes of Selectivity and/or Differentiation that allow making a Quantitative Diagnosis and an effective and Customized Therapy are achieved; it annuls the so-called Hyperthermia effect, caused by all types of radiation used in the state of the technique or in the state of the art for the Therapy Modality, and because it is applied in "Real Time" it nulifies the effects of Overlapping and Cellular Mutability inherent in all living beings as a natural mechanism for survival. The presentation of the so-called "drug resistance" as a natural mechanism for survival of certain pathologies is categorically discarded, since this Invention does not propose the use of drugs as a fundamental part of or as a complement to this Therapy and it only uses Non-Ionizing Electromagnetic Radiations which are adjusted on-line to the evolutive stage of the pathology being treated. In the innovating proposal of this Invention, Non-Ionizing electromagnetic radiations are used instead of Ionizing Radiations, the so-called "Target" Substances are also not used, thus avoiding the problems associated with the Evacuation of these substances from the body.

The Therapy is innocuous as a whole since it does not cause harmful side effects (for example, it does not affect in any way the Nervous and Immune Systems); it significatively reduces the time that passes between Diagnosis, Therapy and Recovery of the patient; the Empiricism that at the moment characterizes the Diagnosis and Therapy Modalities is annulled, except for those Diagnoses where physical-chemical analysis are used and that complement the biopsies and the different test Modalities used to diagnose ine HIV/AIDS.

It significatively reduces the Costs of Research and Development (R+D), as well as those of welfare services.

The Dosimetry Calculation procedures are significantly simplified and they are now exact.

It is a non-invasive application that considerably limits the use of Surgery as a therapeutic modality.

The following Table establishes a comparison, at a qualitative level, between the Existing Technologies (state-of-the-art) and the Technology contained in our Invention so that the potential scope of our Invention can be accurately appraised.

| CHARACTERISTICS TO ANALIZE AND COMPARE | PREVIOUS TECHNOLOGY | | | | PROPOSED TECHNOLOGY | | | |
|---|---|---|---|---|---|---|---|---|
| | DIAGNOSTIC | | THERAPY | | DIAGNOSTIC | | THERAPY | |
| | CANCER | HIV/Aids | CANCER | HIV/Aids | CANCER | HIV/Aids | CANCER | HIV/Aids |
| 1 Selectivity and/or Differentiation | Only on Qualitative level | Solved | With Empiricism | NO | Solved With Quantitative Modality | Introduce Quantitative Modality | Solved With Quantitative Modality | Solved With Quantitative Modality |
| 2 Cellular Overlap | not covered | not covered | Not Solved | Not Solved | Solved | Solved | Solved | Solved |
| 3 Cellular Mutability | not covered | not covered | Not Solved | Not Solved | Solved | Solved | Solved | Solved |
| 4 Types of Radiations employed | Non-Ionizing | Physical-Chemical Analysis | Ionizing >>> Non-Ionizing | Only on a Pharmacological basis | Non-Ionizing | Non-Ionizing + existent | Non-Ionizing | Non-Ionizing |
| 5 "Target Substance" EVACUATION | Eventually | No | In some cases | No | NO | NO | NO | NO |
| 6 Hyperthermia | Eventually | No | Yes | No | Eventually | Eventually, with low impact | Solved | Very Low impact |
| 7 Drug Resistance (in function of # 3) | No | No | Yes Very High | Yes (100%) | NO | NO | NO | NO |
| 8 Harmful Side Effects (in function of # 1) | Relative | Undefined | Yes Very Important | Undefined | NO | NO | NO | NO |
| 9 Index of Empiricism (in function of # 1) | Very High | Solved | High | Very High | NO | NO | NO | NO |
| 10 Surgery (See implications) | Eventually | No | Frequently | No | NO | NO | NO | NO |
| 11 "R + D" Costs | High | Relative Low | Very High | Excessively High | Very Low | Very Low | Very Low | Very Low |
| 12 Implementation on the Health Market | On Long Term | On Long Term | On Long Term | On Long Term | On Short Term | On Short Term | On Short Term | On Short Term |
| 13 Operational Phase of the Project | On Long Term | On Long Term | On Long Term | On Long Term | On Short Term | On Short Term | On Short Term | On Short Term |

Specific Modalities of this Invention have been illustrated and described, it will be obvious for those experts in the technique and/or the art that several modifications or changes can be made without leaving the scope of the Invention. We shall attempt to cover the aforementioned, within the aggregated claims so that all the changes and modifications fall within the scope of this Invention.

Although the Invention has been illustrated and described in detail in the drawings herein attached and in this document, the same has to be considered as illustrative yet non-restrictive and/or limitative in character. It is understood that only the preferred modality has been shown and described; in consequence, we wish to protect all the changes and modifications that are included and/or could be included in the spirit of the Invention.

The invention claimed is:

1. A nuclear magnetic resonance apparatus integrating both the modalities of diagnostic diagnosis and personalized therapy in order to treat pathologies including those generically identified as cancer and HIV/AIDS comprising a magnet with a cooling system and isolation (1), a shim coil system (2), a gradient coil system (3), and a radiofrequency resonation antenna (4) connected to the magnet, a patient table (5), a transmit-receive selector (6) connected to the antenna (4) and a preamplifier (7) connected to the selector (6), radiofrequency and magnetic-proof leadthroughs (8), a radiofrequency low signal processor/quadrature demodulator (9) with low pass filters connected through the leadthroughs (8) to the preamplifier (7), a radiofrequency low signal processor/modulator (10) connected to the radiofrequency low signal processor/quadrature demodulator (9); a radiofrequency pulse amplifier (13) connected to the modulator (10) and to the transmit receive selector (6) through the leadthroughs (8), a magnet power supply (15) connected to the magnet (1) and to the shim coil system (2) through the leadthroughs (8), a central pulse control (16) connected to the radiofrequency low signal processor/quadrature demodulator (9), and also to the radiofrequency low signal processor/modulator (10) by means of analog-digital converters (12), gradient amplifiers X, Y, Z (14) connected by means of digital-analog converters (12) to the central pulse control (16), and also to the shim coil system (2) through the leadthroughs (8), a frequency processor (17) connected to the central pulse control (16), a central computer (20), an image processor (19) connected to the central computer (20), the image processor (19) being also connected to the frequency processor (17), a keyboard (27) connected to the central computer (20), an image storage (21) connected to the central computer (20), an operator's console (22), a protocol monitor (23) connected to the computer (20), an image monitor (24) connected to the image processor (19), a frequency processor (17) connected to the pulse control (16) and to the demodulator (9) by means of analog-digital converters (11), a controlled digital filter/selector and filter (18) connected to the frequency processor (17), a control panel (28) connected to the filter/selector and filter (18), a frequency matrix monitor (25) connected to the frequency processor, and a frequency image monitor (26) connected to the frequency processor (17), wherein the radiofrequency resonation antenna (4), the radiofrequency low signal processor/modulator (10), the radiofrequency pulse amplifier (13), and the central pulse control (16) are adapted for selectively manipulating non-ionizing electromagnetic radiation in order to personalize therapy which treats said pathologies including those generically identified as cancer and HIV/AIDS while eliminating the harmful collateral effect of known hyperthermia, the MRI apparatus integrating both diagnostic and therapy modes in order to treat pathologies as well as quantify diagnostics and selectively manipulate non-ionizing electromagnetic radiation in order to personalize therapy which treats said pathologies including those generically identified as cancer and HIV/AIDS while eliminating the harmful collateral effect of known hyperthermia.

2. The magnetic nuclear resonance apparatus of claim 1, wherein the filter/selector and filter (18), frequency matrix monitor (25), frequency image monitor (26), and control panel (28) have been added to a conventional magnetic nuclear resonance device in order to obtain a quantitative diagnostic.

3. A method of using the magnetic nuclear resonance apparatus of claim 1, comprising creating a highly specialized and differentiated electromagnetic radiation beam with high levels of selectiveness and cellular differentiation for therapy using the radiofrequency resonator antenna (4), radiofrequency low signal processor/modulator (10), radiofrequency pulse amplifier (13); and central pulse control (16).

4. A method of using the magnetic nuclear resonance apparatus of claim 2, comprising obtaining a quantitative diagnostic expressed in terms of the values of composition of the resonance frequency spectrum in the areas of therapeutic interest, in addition to the traditional qualitative result of conventional images, using the filter/selector and filter (18), frequency matrix monitor (25), frequency image monitor (26), and control panel (28).

5. The magnetic nuclear resonance apparatus of claim 2, wherein the frequency matrix monitor (25) allows the specific, particular and respective values of the resonance frequencies of the areas of therapeutic interest to he accurately known and the frequency image monitor (26) provides information in image and graphic format that is a direct function of the resonance frequencies and provides a profile of the resonance frequencies of the studied area, allowing a modality of quantitative diagnosis.

6. The method of claim 4, further comprising creating a highly specialized and differentiated electromagnetic radiation beam based on the quantitative diagnostic with high levels of selectiveness and cellular differentiation for therapy using the radiofrequency resonator antenna (4), radiofrequency low signal processor/modulator (10), radiofrequency pulse amplifier (13), and central pulse control (16), and using the radiation beam to destroy a detected pathology while annulling hyperthermia and maintaining bioenergetics equilibrium in the area of therapeutic interest.

7. The method of claim 5, further comprising creating a highly specialized and differentiated electromagnetic radiation beam with high levels of selectiveness and cellular differentiation for therapy using the radio frequency resonator antenna (4), radiofrequency low signal processor/modulator (10), radiofrequency pulse amplifier (13), and central pulse control (16), wherein the radiation beam is created in real time based on previous selective manipulation of frequency, power, and polarity parameters of the non-ionizing electromagnetic emission used in the quantitative diagnosis modality, providing a therapy that is personalized because it fits to the area of therapeutic interest in an exact and current way.

8. The method of claim 7, wherein the radiation beam is a continuous pulse sequence.

9. The method of claim 4, further comprising creating a highly specialized and differentiated electromagnetic radiation beam with high levels of selectiveness and cellular differentiation for therapy using the radiofrequency resonator antenna (4), radiofrequency low signal processor/modulator (10), radiofrequency pulse amplifier (13), and central pulse control (16), wherein the radiation beam, in addition to a resonance frequency series designed to eliminate a pathology, contains another series of resonance frequencies determined from the quantitative diagnostic that allows for evacuation by physical means of the excess heat/energy generated by hyperthermia, which affects surrounding healthy tissue, which can be continuous or alternate according to therapeutic interest and energy behavior of the area of study.

* * * * *